(12) United States Patent
Bassan et al.

(10) Patent No.: US 8,602,980 B2
(45) Date of Patent: Dec. 10, 2013

(54) FOLDING ENDOSCOPE AND METHOD OF USING THE SAME

(75) Inventors: Harmanpreet Bassan, Toronto (CA); Peter Kim, Totonto (CA); Thomas Looi, Markham (CA)

(73) Assignee: The Hospital for Sick Children, Toronto, ON (CA)

( * ) Notice: Subject to any disclaimer, the term of this patent is extended or adjusted under 35 U.S.C. 154(b) by 160 days.

(21) Appl. No.: 13/158,072

(22) Filed: Jun. 10, 2011

(65) Prior Publication Data

US 2011/0306832 A1 Dec. 15, 2011

Related U.S. Application Data

(60) Provisional application No. 61/353,948, filed on Jun. 11, 2010.

(51) Int. Cl.
*A61B 1/05* (2006.01)
*A61B 1/07* (2006.01)
*A61B 1/00* (2006.01)
*A61B 1/06* (2006.01)

(52) U.S. Cl.
CPC ......... *A61B 1/00183* (2013.01); *A61B 1/00193* (2013.01); *A61B 1/0676* (2013.01); *A61B 1/07* (2013.01)
USPC ............ 600/173; 600/166; 600/129; 600/179

(58) Field of Classification Search
USPC ......... 600/109, 129, 111, 160, 170, 171, 173, 600/166, 179; 356/241.3, 241.5
See application file for complete search history.

(56) References Cited

U.S. PATENT DOCUMENTS

| | | | | |
|---|---|---|---|---|
| 4,862,873 A | | 9/1989 | Yajima et al. | |
| 5,166,787 A | * | 11/1992 | Irion | 348/75 |
| 5,305,121 A | * | 4/1994 | Moll | 348/45 |
| 5,368,015 A | * | 11/1994 | Wilk | 600/104 |
| 5,381,784 A | * | 1/1995 | Adair | 600/166 |
| 6,066,090 A | * | 5/2000 | Yoon | 600/113 |
| 6,261,226 B1 | * | 7/2001 | McKenna et al. | 600/109 |
| 7,029,435 B2 | * | 4/2006 | Nakao | 600/153 |
| 7,601,119 B2 | * | 10/2009 | Shahinian | 600/111 |
| 7,751,870 B2 | * | 7/2010 | Whitman | 600/476 |
| 7,927,272 B2 | * | 4/2011 | Bayer et al. | 600/129 |
| 8,277,373 B2 | * | 10/2012 | Maahs et al. | 600/107 |
| 2002/0007110 A1 | | 1/2002 | Irion | |

(Continued)

*Primary Examiner* — John P Leubecker
(74) *Attorney, Agent, or Firm* — Lynn C. Schumacher; Hill & Schumacher

(57) ABSTRACT

A folding endoscope with incorporated optical sensors and light sources includes a housing having first and second ends and a longitudinal axis and at least one channel extending between the first and second ends and associated ports at the first and second ends for inserting surgical instruments through the housing into a surgical site. The endoscope includes at least two elongate arms having proximal and distal ends and being pivotally connected at the distal ends thereof to the first end of the housing. A camera and light source are mounted on each of the elongate arms such that when the elongate arms are deployed the cameras have a field of view in a generally forward direction away from the housing. A linkage mechanism is connected to the elongate arms, and an actuator is connected to the linkage mechanism. The linkage mechanism, upon activation by the actuator, is configured to pivotally deploy the at least two elongate arms from a closed position in which the elongate arms are aligned along the longitudinal axis to an open position with the distal ends of the elongate arms radially spaced from the longitudinal axis.

18 Claims, 4 Drawing Sheets

(56) References Cited

U.S. PATENT DOCUMENTS

| | | | |
|---|---|---|---|
| 2002/0049367 A1* | 4/2002 | Irion et al. ............. | 600/173 |
| 2005/0234296 A1* | 10/2005 | Saadat et al. ........... | 600/129 |
| 2006/0252994 A1* | 11/2006 | Ratnakar ................. | 600/173 |
| 2007/0032701 A1* | 2/2007 | Fowler et al. ........... | 600/173 |
| 2007/0073109 A1* | 3/2007 | Irion ...................... | 600/179 |
| 2008/0027279 A1* | 1/2008 | Abou El Kheir ........ | 600/111 |
| 2008/0071288 A1* | 3/2008 | Larkin et al. ........... | 606/130 |
| 2009/0030276 A1* | 1/2009 | Saadat et al. ........... | 600/112 |
| 2010/0081875 A1* | 4/2010 | Fowler et al. ........... | 600/114 |
| 2010/0249512 A1* | 9/2010 | McKinley et al. ....... | 600/160 |

\* cited by examiner

FOLDING ENDOSCOPE AND METHOD OF USING THE SAME

CROSS REFERENCE TO RELATED U.S. PATENT APPLICATION

This patent application relates to U.S. provisional patent application Ser. No. 61/353,948 filed on 11 Jun. 2010 entitled FOLDING ENDOSCOPE AND METHOD OF USING THE SAME, filed in English, which is incorporated herein in its entirety by reference.

FIELD OF THE INVENTION

The present invention relates generally to the field of endoscopes, and more particularly the present invention relates to folding endoscopes with incorporated optical sensors and light source.

BACKGROUND OF THE INVENTION

Generally speaking, endoscopes are thin tubular cameras that are typically utilized in the diagnosis of a disease. These cameras are usually inserted into the body cavity either through a natural opening like the mouth or the anus or through a tiny incision made into the skin. The endoscopes are extensively used intra-operatively to assist the surgeon in visualizing the anatomy of interest to perform the procedure and to avoid damage to critical surrounding organs. Most of the endoscopes available in the market to date can be classified into either a rigid or a flexible endoscope. Commonly found endoscopes are available with two-dimensional cameras and have limited image resolution and depth perception. These endoscopes are disorienting to the surgeon after a prolonged use and lack the natural spectrum of direct human visualization.

Recently some manufacturers have started producing three-dimensional (stereoscopic) endoscopes. The optical version of these endoscopes use two tubular lenses inside a long shaft and two standard cameras mounted outside of the body. The next generation of stereo endoscopes employs custom designed semiconductor circuitry mounted at the tip of the endoscope (inside the body) that is capable of producing stereo images. In these endoscopes, either two close proximity mounted chips or a special chip with a large array of micro lenses manufactured onto the chip is utilized to create stereo images. In addition, such endoscopes also include LED or fiber optic light sources for illumination. FIG. 1 shows a conventional stereo endoscope.

U.S. Pat. No. 4,862,873 issued to Yajima et al. discloses a stereo endoscope that utilizes two thin optical guides mounted in a tubular shaft and two CCD image sensors mounted outside the body to create three-dimensional images of the organ.

U.S. Patent application US2002/0007110, to Irion discloses a stereo endoscope that utilizes two lateral mounted cameras with a flexible endoscope head to create three-dimensional images of the organ.

The field of surgical intervention has evolved from open invasive approach to the paradigm of minimally invasive surgery due to its benefits to the patients and the healthcare system. From the surgeon's perspective, the transition has resulted in a procedure with limited and un-natural field of view and surgical skills that have a steep learning curve. The existing three-dimensional endoscopes have resulted in incremental enhancement to the visualization, but have failed to match the natural spectrum of direct human visualization. The 3D depth perception of these endoscopes is also constrained by the limited physical separation between the two cameras. Additionally, it is projected that the surgical paradigm will shift from the three or four incision laparoscopic approach to a single incision (single port access (SPA)) surgery.

Thus, there is a need and good market potential for improved endoscopes that can provide a better visualization of the surgical site.

SUMMARY OF THE INVENTION

The present invention provides a foldable endoscope, comprising:
a) a housing having a first and second end and a longitudinal axis, said housing including at least one channel extending between said first and second end, and associated ports at said first and second end for inserting surgical instruments through said housing into a surgical site;
b) at least two elongate arms each having a first and second end and each being pivotally connected at said first end thereof to said first end of said housing;
c) at least one camera each camera being mounted on one of said at least two elongate arms; and
d) a linkage mechanism connected to said at least two elongate arms, said linkage mechanism, upon activation, being configured to pivotally deploy said at least two elongate arms from a closed position in which said at least two elongate arms are aligned along said longitudinal axis to an open position in which said second ends of said at least two elongate arms radially spaced from said longitudinal axis.

The disclosed endoscope taps nicely into the emerging market due to its improved visualization capabilities and integrated support to pass surgical tools through the other ports making it a versatile surgical tool.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Without limitation, the majority of the systems described herein are directed to folding endoscopes with incorporated optical sensors and light source. As required, embodiments of folding endoscopes are disclosed herein. However, the disclosed embodiments are merely exemplary, and it should be understood that the disclosure may be embodied in many various and alternative forms. In certain instances, wellknown or conventional details are not described in order to provide a concise discussion of embodiments of the present disclosure.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to folding endoscopes with incorporated optical sensors and light source.

As used herein, the term "about" and "approximately", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions of components of a folding endoscope are given but it will be understood that these are not meant to be limiting.

Figure 1:
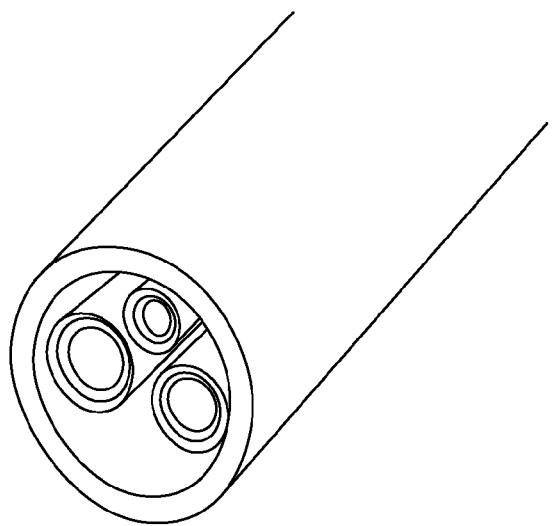
FIG. 1 shows a conventional prior art stereo endoscope.
Figure 2:
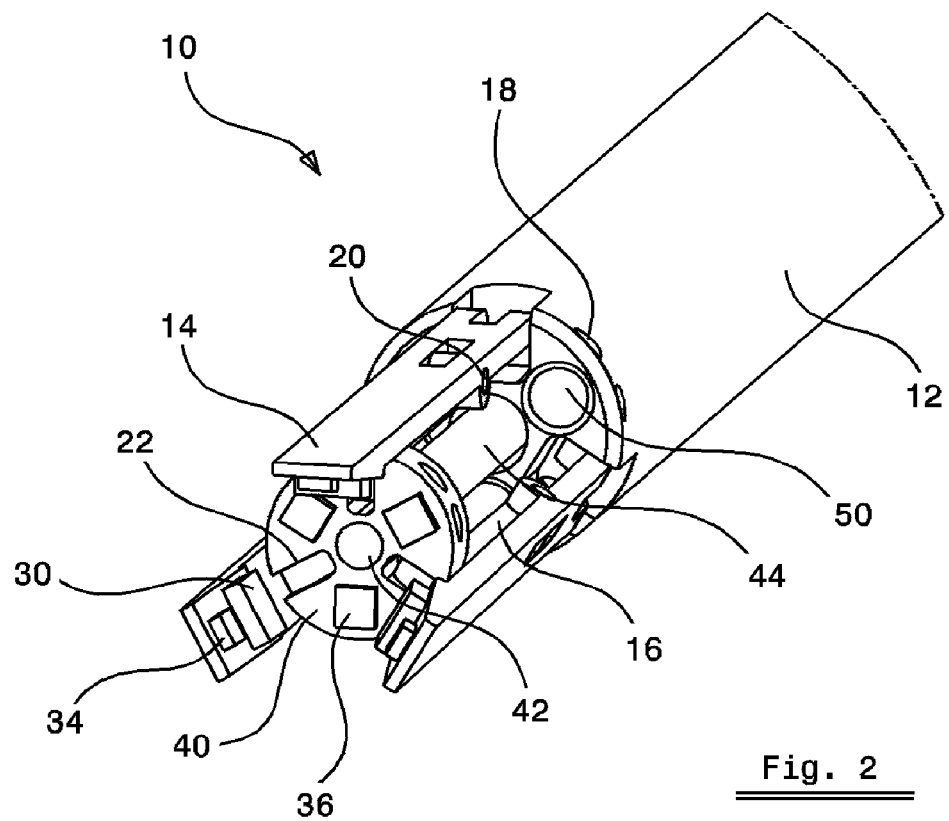
FIG. 2 shows an embodiment of the foldable endoscope in a fully closed or retracted state.
Figure 3:
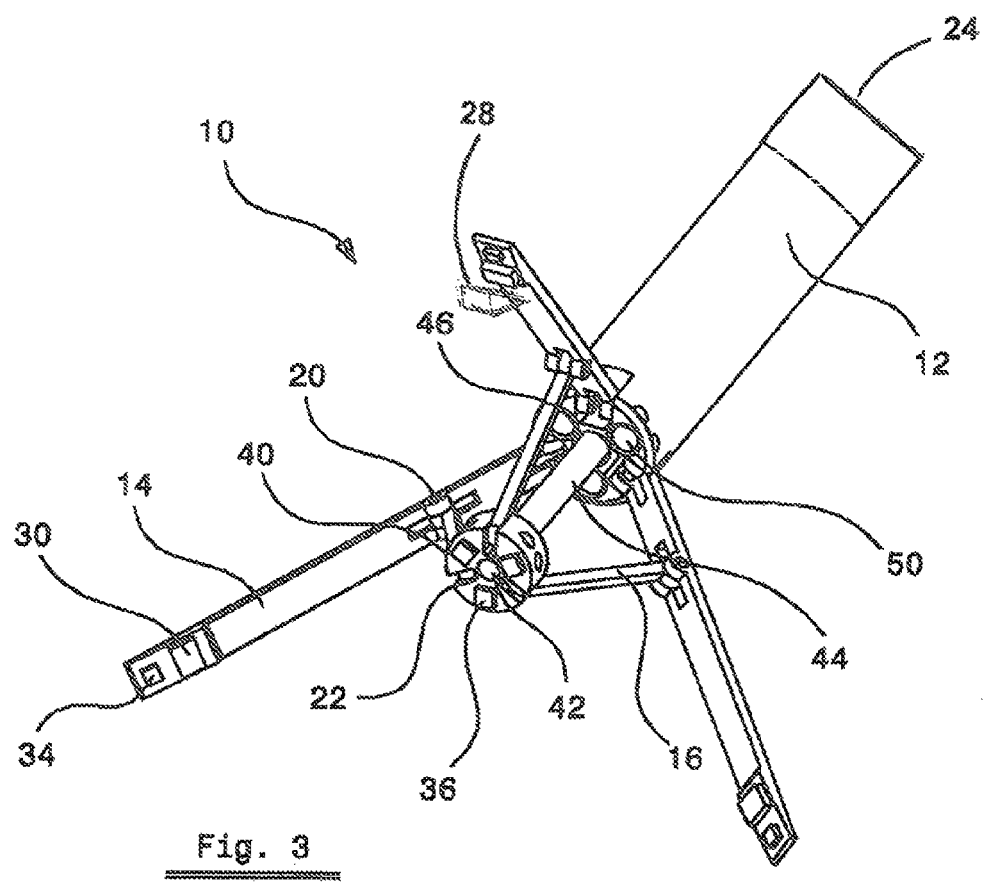
FIG. 3 shows the foldable endoscope in a partially open state.

Referring to FIG. 2, herein is disclosed a foldable endoscope 10 that utilizes multiple cameras 30 to create three-dimensional images of the target. FIG. 2 shows the endoscope 10 in collapsed form, and FIG. 3 shows the endoscope 10 in half open form. In the collapsed form, the endoscope 10 assumes a very compact formation and can be easily introduced into the patient's body through a standard trocar. In the preferred embodiment, the endoscope 10 contains a slender body 12 that forms a generally cylindrical housing, a center spoke 40, three connecting linkages 16, and three folding arms 14 with cameras 30 and light sources 34 integrated into each of the arms. Each folding arm 14 in the preferred embodiment includes two hinge joints; a first hinge joint 18 with the endoscope body 12 and a second hinge joint 20 with the connecting linkage 16. In the preferred embodiment, each connecting linkage 16 also has a hinge joint 22 with the center spoke 40. The center spoke 40 includes a telescopingly movable hollow drive shaft 44 and may optionally include a plurality of integrated light sources 36 (light emitting diodes (LEDs), fiber optic light sources, etc).

The optical sensors or cameras are preferably charge coupled device (CCD) images sensors, but other types of image sensors may be used. For example, complementary metal-oxide-semiconductor (CMOS) image sensors may be preferred in some embodiments due to their low cost.

The endoscope 10 also includes one or more instrument ports 50 through which various surgical instruments can be introduced to perform the procedure. Non-limiting examples of such instruments include scalpels, incision devices, tweezers, scissors, etc. In the preferred embodiment, the diameter of slender body 12 is preferably about 10 mm and the diameter of each instrument port 50 is preferably about 2.5 mm. The disclosed invention is particularly suitable for the case of a single port access surgery where both the visualization and the surgical procedure is performed through one incision as opposed to the three or four of a typical laparoscopic procedure. Endoscope 10 may optionally include a fiber optic illumination port 42 mounted on the center spoke 40 to enhance visibility of the surgical site. In the preferred embodiment, the diameter of fiber optic illumination port 42 is preferably about 1.75 mm. The fiber optic illumination port 42 is a hollow shaft that runs concentrically through the center spoke 40 and the hollow drive shaft 44.

FIG. 3 shows the preferred embodiment of the disclosed invention in the half open form. The hollow drive shaft 44 is designed to translate in and out through the center port 46 of the endoscope body 12. Here "in" motion is referred to as the motion of the center spoke 40 towards the endoscope body 12 and "out" motion is referred to as the motion of the center spoke 40 away from the endoscope body 12. Each hinge joint (18, 20, and 22) is a low friction joint that allows two mating components to freely rotate with respect to each other about the hinge axis. A hollow drive shaft 44 is connected on one end to the center spoke 40 and is connected at the other end to the endoscope body 12 to create the linear "in" and "out" motion of the center spoke 40 with respect to the endoscope body 12. In a preferred embodiment, this motion is provided by an actuator 24 (preferably located outside the body). Those skilled in the art will appreciate that any actuator 24 may be used; some non-limiting examples include solenoids, motors with rack and pinion gears, hydraulic actuators, pneumatic actuators, cable actuators, worm gears, and wheels with tracks.

A fiber optic illumination source may be passed through the hollow shaft 44 to enhance visibility of the surgical site. Optionally, one of more of the illumination sources 36 on the center spoke 40 may be replaced with one or more cameras 30 that can facilitate easy insertion of the endoscope into patient's body cavity.

Figure 4:
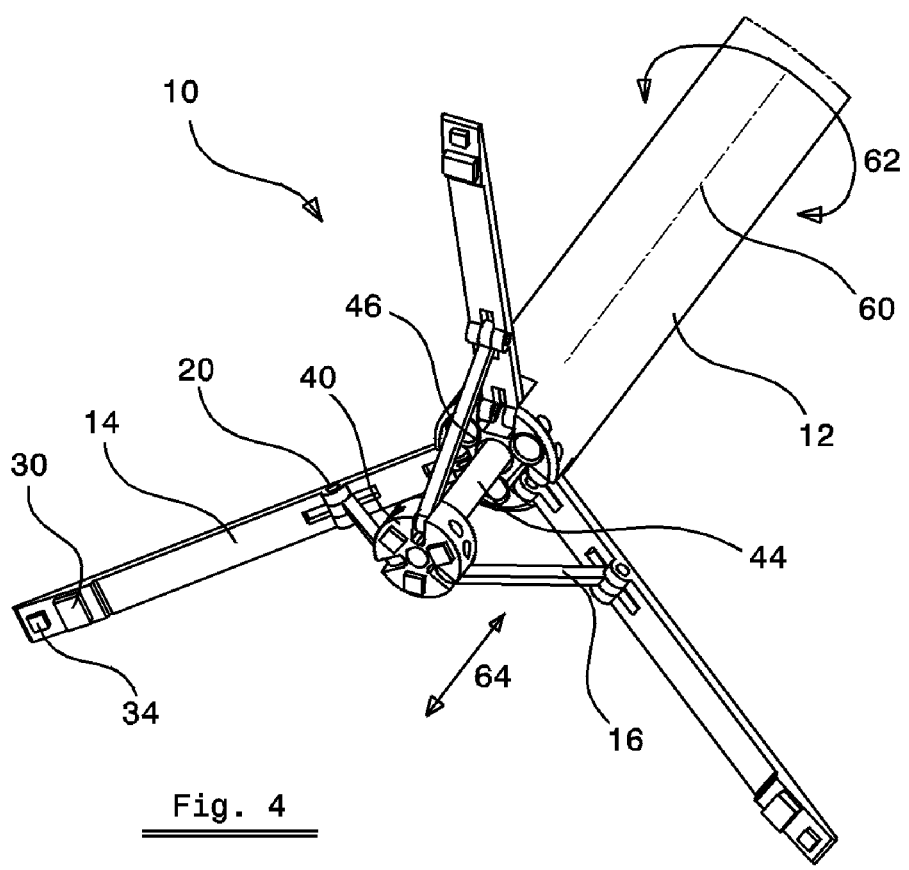
FIG. 4 shows the foldable endoscope in the fully open state.

One preferred method of utilizing the disclosed invention in a single port access surgery can be as following. Initially with the endoscope 10 outside the body, the hollow shaft 44 is actuated such that the center spoke 40 is at its farthest "out" position and as a result the endoscope is fully collapsed (as shown in FIG. 2) and can be easily introduced into the patient's body through a standard trocar. Once inside the body, the hollow shaft 44 is actuated to cause "in" motion of the center spoke 40 towards the endoscope body 12. The umbrella structure of the mechanism causes it to unfold and gradually take up its open shape as the center spoke 40 is actuated towards the fully "in" position (as shown in FIG. 4). The tile angle for cameras 30 can be simultaneously controlled by "in" and "out" motions of the center spoke 40 in the direction of arrow 64. The actuator is used to control how much the umbrella structure opens up, and this depends on the user of endoscope and how much overlap is required between the cameras 30.

Once fully deployed, endoscope 10 can be firmly held in place (outside the body) by an assistant, a passive support arm, or a robotic system. The endoscope 10 can also be rolled through the use of an optional second actuator about axis 60 in the direction of arrows 62 until desired visualization of the anatomy is achieved.

Figure 5:
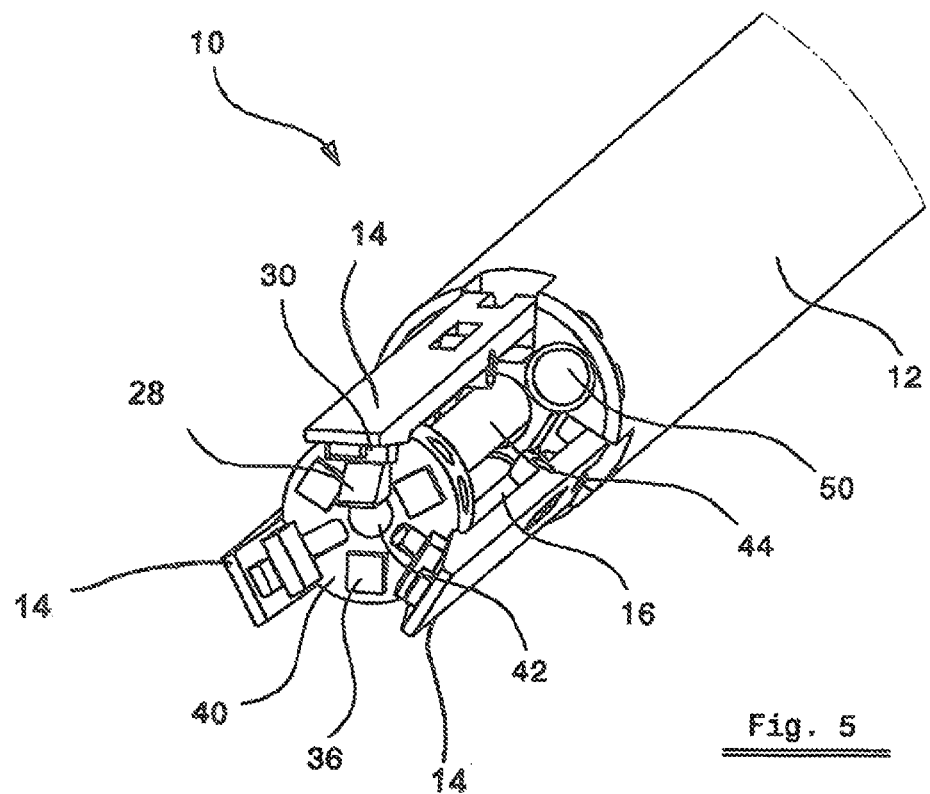
FIG. 5 shows another embodiment of the foldable endoscope that includes a mirror arrangement.

FIG. 5 shows another embodiment of the foldable endoscope that includes a mirror arrangement 28 that assists in the insertion of the endoscope into the body cavity. In its collapsed form (as shown), the mirror 28 is mounted on one of the elongate arms 14 for reflecting light into the camera 30 mounted on the elongate arm 14 and is oriented such that it reflects light rays that are parallel to the longitudinal axis of endoscope body 12 onto the image sensor 30 thereby creating an image that is orthogonal to the endoscope longitudinal axis. This image is the same image as obtained using the conventional endoscopes as they are being inserted into the body cavity. Once inside the body and after the mechanism has been unfolded, mirror 28 has no function and the endoscope creates 3D images as explained before. This mirror arrangement obviates the need of another 2D image sensor on the center spoke 40 that can assist in endoscope insertion through the trocar.

Figure 6:
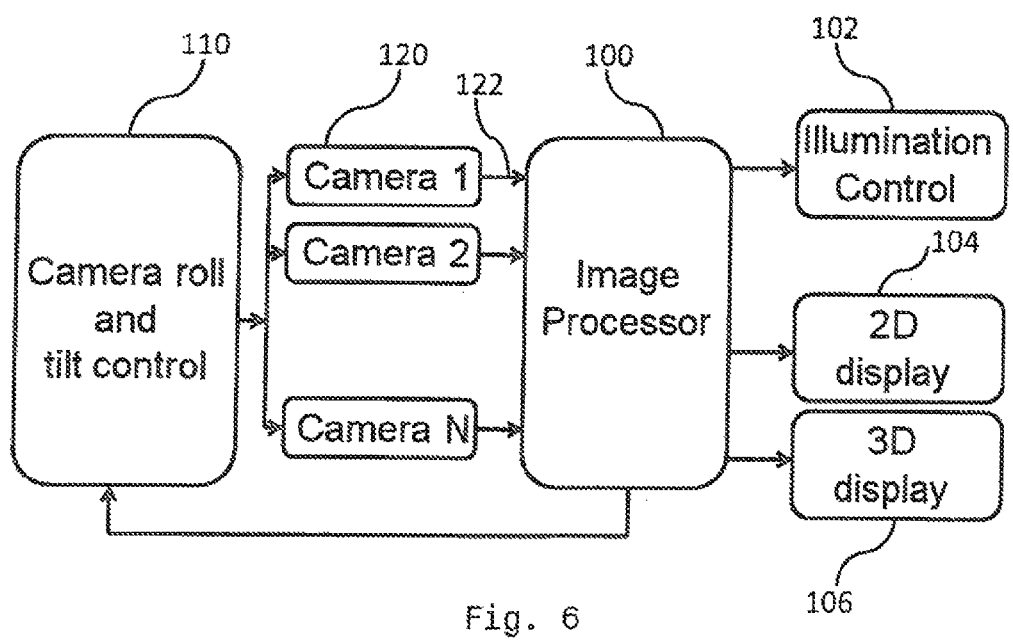
FIG. 6 shows the block diagram of the image processing of the images acquired by the cameras mounted on the foldable endoscope.

FIG. 6 shows the block diagram of the disclosed invention. The video outputs 122 from various cameras 120 go to an image processor 100 that performs various image processing algorithms for example stereo generation, image stitching etc. on these images. The processed images are provided to the surgeon's in either a two-dimensional or a three-dimensional format through the use of a display device 104 or 106 (monitor, projector, 3D monitor, 3D goggles, etc). The image processor 100 may also control camera tilt and roll system 110 in order to generate a view from a different orientation and perspective. The roll and tilt system is preferably composed of two actuators that cause the linear motion of center spoke 40 along arrows 64 and roll of body 12 about axis 60 (as shown by arrow 62). Depending upon the anatomy, the image processor may also control the illumination system 102 to adjust for optimal image quality. The illumination system 102 may automatically adjust camera parameters based on feedback from image signals received from the cameras. The illumination system 102 may include any manual input device such as a physical button, knob, or slider, or it may be a graphical user interface element displayed on a monitor. Further, when producing three-dimensional images, the image processor 100 may further rotate, translate, and scale the produced images either by decisions made from software control systems or from manual control from the user, or both.

The surgeon may interact with the image processor 100 through a user interface that includes an input device (computer mouse, keyboard, microphone, buttons, joystick, touch screen etc) to select various features and options. The surgeon can optionally switch between two-dimensional and three-dimensional views or can visualize them side by side on displays 104 and 106. The surgeon may use the user interface to change views, to change brightness or contrast parameters, to rotate, scale, or translate 3D views, or to make other parameter changes that influences the display shown on monitors.

Those skilled in the art will appreciate that many computer vision algorithms may be performed by the image processor 100 including but not limited to: image stitching, 3D reconstruction from multiple views, shape from shading, depth from focus, feature detection, feature matching for pose estimation, optical flow algorithms, background subtraction, automatic object classification, and image segmentation. These techniques may be used to assist the user of the endoscope in performing operations with the device. Further, those skilled in the art that the image processor 100 may be a dedicated computer processor such as a CPU, DSP microchip, or microprocessor, or the image processor 100 may be integrated in a computer system such as a software program running on a desktop computer, laptop, mobile device, or mobile phone.

The disclosed invention utilizes an umbrella type mechanism to mount and control one or more cameras (preferable two or more) that is not found in conventional two-dimensional and three-dimensional endoscopes. The increased physical separation between different cameras of the disclosed invention will lead to an improved 3D depth perception than that of the close mounted dual cameras in the existing systems. The increased number of cameras (preferably three or more) present in the disclosed invention will lead to enhanced visualization of the anatomy through image stitching. The mechanism disclosed herein is fairly simple and low cost to produce. The number of folding arms can be limited to two if reduced cost or functionality is desired.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A foldable endoscope, comprising:
   a) a housing having a first and second end and a longitudinal axis, said housing including at least one channel extending between said first and second end, and associated ports at said first and second end for inserting surgical instruments through said housing into a surgical site;
   b) at least two elongate arms each having a proximal and distal end and each being pivotally connected at said proximal end thereof to said first end of said housing to form at least two pivot connections, each of said at least two elongate arms having at least one light source mounted thereon;
   c) at least one camera, said at least one camera being mounted on one of said at least two elongate arms adjacent to said distal end thereof;
   d) a linkage mechanism connected to said at least two elongate arms, said linkage mechanism, upon activation, being configured to pivotally deploy said at least two elongate arms about said at least two pivot connections such that each distal end pivots about its associated proximal end pivot connection to said housing, from a closed position in which said at least two elongate arms are aligned along said housing to an open position in which said distal ends are radially spaced from said housing; and
   e) an actuator connected to said linkage mechanism, said actuator capable of activating said linkage mechanism, said housing including a center passageway extending through said housing, and wherein said linkage mechanism includes a center spoke connected to a first end of a hollow drive shaft telescopingly movable in and out of said center passageway through a center port at said first end of said housing, said actuator being connected to a second opposed end of said hollow drive shaft.

2. The foldable endoscope according to claim 1, wherein said at least one camera is arranged such that when said at least two elongate arms are deployed, said at least one camera has a field of view that includes a generally forward direction away from said housing.

3. The foldable endoscope according to claim 1 wherein said at least two elongate arms is three elongate arms.

4. The foldable endoscope according to claim 1 wherein said at least one camera is at least two cameras, each camera being mounted on one of said at least two elongate arms.

5. The foldable endoscope according to claim 1 wherein each of said at least two elongate arms has a linkage arm pivotally connected at one end of said linkage arm to the elongate arm, the other end of said linkage arm being pivotally connected to said center spoke, wherein upon actuation of said actuator to move said hollow drive shaft into said center passageway drawing said center spoke towards said first end of said housing causes said linkage arms to force said at least two elongate arms to pivot about their pivot connections at said first end of said housing thereby pushing said second end of said at least two elongate arms radially outward.

6. The foldable endoscope according to claim 5 wherein said linkage arm is pivotally connected at each end thereof with hinges.

7. The foldable endoscope according to claim 1 wherein said actuator is a linear actuator.

8. The foldable endoscope according to claim 1 further including a mirror mounted on one of said at least two elongate arms for reflecting light into the camera mounted on said one of said at least two elongate arms.

9. The foldable endoscope according to claim 8 wherein said mirror is oriented such that said mirror reflects light rays that are generally parallel to said longitudinal axis into the camera mounted on said one of said at least two elongate arms.

10. The foldable endoscope according to claim 1 wherein said center spoke includes a plurality of light sources mounted thereon.

11. The foldable endoscope according to claim 10 wherein said plurality of light sources are one or both of light emitting diodes and optical fibers optically coupled to an external light source.

12. The foldable endoscope according to claim 1 wherein said center spoke includes a fiber optic illumination port mounted thereon to enhance visibility of said surgical site into which the foldable endoscope is inserted, the light being transmitted to said fiber optic illumination port by an optical fiber extending through said hollow drive shaft and through said center passageway and being connected to a light source.

13. The foldable endoscope according to claim 1 wherein said center spoke includes a camera mounted thereon facing away from said housing.

14. The foldable endoscope according to claim 1 wherein said housing is a cylindrical housing.

15. The foldable endoscope according to claim 1 wherein said at least one camera is two or more cameras each mounted on a separate elongate arm and configured to provide a field of view from which three-dimensional images of said surgical site can be produced.

16. The foldable endoscope according to claim 15 including an image processor, each camera having an output that is connected to said image processor and said image processor being connected to an image display device, said image processor including image processing algorithms for presenting images to said image display device.

17. The foldable endoscope according to claim 16 including a tilt and roll system connected to said housing, and wherein said image processor is configured to control said tilt and roll system in order to generate a view from different orientations and perspectives, and said image processor being configured to provide processed images to a user in either a two-dimensional or a three-dimensional format.

18. The foldable endoscope according to claim 17 including a user interface connected to said image processor configured to allow said user to interact with said image processor through an input device to select features and options, and to allow said user to switch between two-dimensional and three-dimensional views or visualize said views side by side on said image display device.

* * * * *